(12) United States Patent
Connor (10) Patent No.: US 8,306,237 B2
(45) Date of Patent: Nov. 6, 2012

(54) HEAD-MOUNTING DEVICE TO MASK AMBIENT SOUNDS FOR SLEEPING

(75) Inventor: Robert A. Connor, Minneapolis, MN (US)

(73) Assignee: Medibotics, Forest Lake, MN (US)

( * ) Notice: Subject to any disclaimer, the term of this patent is extended or adjusted under 35 U.S.C. 154(b) by 283 days.

(21) Appl. No.: 12/799,155

(22) Filed: Apr. 20, 2010

(65) Prior Publication Data

US 2011/0257469 A1    Oct. 20, 2011

(51) Int. Cl.
*H04R 3/02*    (2006.01)
*H04R 25/00*    (2006.01)

(52) U.S. Cl. .................. 381/73.1; 381/376; 381/382

(58) Field of Classification Search .......... 381/74, 381/309, 311, 77, 78, 333, 334, 71.6, 73.1, 381/72, 370, 376, 382
See application file for complete search history.

(56) References Cited

U.S. PATENT DOCUMENTS

| | | | |
|---|---|---|---|
| 3,539,031 A | 11/1970 | Scanlon | |
| 3,728,741 A | 4/1973 | Lepor | |
| 3,899,044 A | 8/1975 | Stumpf et al. | |
| 3,939,310 A | 2/1976 | Hodges | |
| 3,993,879 A * | 11/1976 | Larkin | 379/430 |
| 4,070,553 A | 1/1978 | Hass | |
| 4,110,583 A | 8/1978 | Lepper | |
| 4,173,715 A | 11/1979 | Gosman | |
| 4,261,432 A | 4/1981 | Gunterman | |
| 4,347,911 A | 9/1982 | Bertagna et al. | |
| 4,424,880 A | 1/1984 | Murayama et al. | |
| 4,554,993 A | 11/1985 | Houng | |
| 4,776,044 A | 10/1988 | Makins | |
| 4,864,619 A | 9/1989 | Spates | |
| 5,022,486 A | 6/1991 | Miura et al. | |
| 5,303,426 A | 4/1994 | Jones | |
| 5,625,903 A | 5/1997 | Schultz et al. | |
| 5,631,965 A | 5/1997 | Chang et al. | |
| 5,824,967 A | 10/1998 | Zwislocki | |
| 5,844,996 A | 12/1998 | Enzmann et al. | |
| 5,881,390 A * | 3/1999 | Young | 2/209.13 |
| 5,953,434 A | 9/1999 | Boyden | |
| 6,014,345 A | 1/2000 | Schmadeka | |
| 6,289,538 B1 | 9/2001 | Fidge | |
| 6,301,367 B1 | 10/2001 | Boyden et al. | |
| 6,567,525 B1 | 5/2003 | Sapiejewski | |
| 6,826,287 B2 | 11/2004 | Myers | |
| 6,920,228 B2 | 7/2005 | Redmer et al. | |
| 7,006,650 B1 | 2/2006 | Wild | |

(Continued)

FOREIGN PATENT DOCUMENTS

WO    WO 2009141578 A1 * 11/2009

*Primary Examiner* — Ping Lee (57) ABSTRACT

This invention is a wearable device that masks and/or cancels annoying ambient sounds to help a person sleep. It includes a soft and stretchable member, such as a headband or hat, that contains one or more sound-conducting tubes. Sound that is emitted from the one or more tubes helps to mask and/or cancel annoying ambient sounds. Advantages of this device over prior art include: no speakers or other rigid components over a person's ears that can be uncomfortable or unsafe when the person sleeps on their side; a relatively wide sound-emitting area to accommodate different size and shape heads; and a stretchable wearable member that gently clings to the person's head to avoid having sound-emitting areas shift away from the person's ears as they toss and turn in their sleep.

20 Claims, 5 Drawing Sheets

U.S. PATENT DOCUMENTS

| | | |
|---|---|---|
| 7,024,013 B1 | 4/2006 | Van Dam et al. |
| 7,110,563 B2 | 9/2006 | Bergere |
| 7,248,705 B1 | 7/2007 | Mishan |
| 7,268,669 B2 | 9/2007 | McEvoy |
| 7,340,071 B2 | 3/2008 | Huang |
| 7,394,912 B2 | 7/2008 | Whipple |
| 7,627,917 B2 | 12/2009 | Vandenbelt |
| 2005/0070823 A1* | 3/2005 | Donofrio et al. .............. 600/595 |
| 2007/0280484 A1 | 12/2007 | Anderson |
| 2008/0304691 A1 | 12/2008 | Lai |
| 2009/0257615 A1* | 10/2009 | Bayer, Jr. ...................... 381/376 |

* cited by examiner

HEAD-MOUNTING DEVICE TO MASK AMBIENT SOUNDS FOR SLEEPING

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND

1. Field of Invention

This invention relates to wearable sound-emitting devices that mask or cancel ambient sounds to help someone to sleep.

2. Introduction

Many people live in places that are increasingly noisy. The modern world is permeated by: intrusive sound systems with powerful bass speakers that penetrate apartment walls, video games with loud explosions and sound effects, vehicles with thumping bass speakers, jet and train traffic at all hours of the day and night, sirens and heavy equipment, dogs that bark incessantly, and so forth. The list of noise pollution sources grows each year. High noise levels are bad enough during daylight hours, but can be especially devastating at night when one is trying to sleep. Lack of sleep due to ambient sounds can wreak havoc on one's health, productivity, and overall quality of life. Sleep-disturbing sounds can even come from one's own household. For example, loud snoring can have devastating effects on one's closest personal relationships.

Some people can afford to live in places that are far removed from the flight paths of major airports, but other people cannot. Some people can afford to live far away from establishments that play loud music until the early morning hours, but other people cannot. Some people can afford to have living arrangements with multiple bedrooms so that they do not have to choose between a close relationship and getting enough sleep to face the next day, but other people cannot. For many people, sleep deprivation is a vicious cycle. Sleep deprivation hinders them from earning more income, the limited income limits their living options, and the limited living options result in more sleep deprivation. What can be done to break this cycle to help people to get a decent night's sleep in today's increasingly noisy world?

There is some prior art that is intended to reduce a sleeper's disturbance from ambient sounds. Much of this prior art involves sound "blocking," sound "masking," and/or sound "cancellation." Sound "blocking" uses sound-insulating layers or structures to impede sound conduction and reduce the amount of ambient sound that reaches a sleeper's ears. Sound "masking" involves playing sounds to cover up ambient sounds. Many sound-masking devices create sounds with a broad-spectrum of frequencies, such as "white noise" or "pink noise," to cover up ambient sounds at random. Other sound-masking devices offer a menu of sounds from which the sleeper can select to cover up particular ambient sounds.

Sound "cancellation" involves monitoring ambient sounds and custom-generating sounds that have a symmetrically-opposite wave structure to the ambient sounds. Ideally, when the ambient sound waves and the custom-generated sound waves overlap, their acoustic energies cancel each other out because their wave patterns are symmetrically opposite to each other. However, as we will discuss, the prior art in the area has significant limitations. There remains an unmet need for innovative devices to block, mask, or cancel ambient sounds to enable people to have a good night's sleep in noisy environments.

SUMMARY AND LIMITATIONS OF THE PRIOR ART

The relevant prior art for reducing sleeper's disturbance from ambient sounds may be categorized into five general categories: (1) devices that are worn to block (but not mask or cancel) ambient sounds; (2) devices that mask or cancel ambient sounds, but are not worn; (3) relatively rigid headphones or ear buds that are worn to mask or cancel ambient sounds, but are not designed to be worn while sleeping; (4) devices that include a sound-emitting acoustic tube that fits into a person's ear, but are not designed to be worn while sleeping; and (5) a soft headband or hat that contains speakers placed over the ears, that can be worn while sleeping. We now briefly discuss each of these device categories, including some examples from the prior art and their limitations. Afterwards, we discuss how these limitations are addressed by the invention disclosed herein.

1. Wearable Devices that Block (but do not Mask or Cancel) Ambient Sounds

The prior art includes devices that are worn to block (but not mask or cancel) ambient sounds. These devices often use insulating layers or structures to impede the conduction of sound waves. They reduce the amount of ambient sound that reaches a sleeping person's ears. Examples of wearable sound-blocking devices include ear plugs and ear muffs. Examples of devices in the prior art that appear to be in this category include U.S. Pat. Nos. 3,728,741 (Lepor, 1973), 6,826,287 (Myers, 2004), 7,006,650 (Wild, 2006), and 7,024,013 (Van Dam et al., 2006). Limitations of such devices can include: such devices can be less effective for reducing awareness of ambient sounds than devices that actively emit sound to mask or cancel ambient sounds; such devices do not address tinnitus (ringing in the ears) wherein the "source" of the sound is internal to the ear and is made worse by blocking external sounds; and devices with rigid components can have adverse safety and comfort issues when a sleeper tosses and turns in their sleep.

2. Devices that Mask or Cancel Ambient Sounds, but are not Worn

The prior art also includes devices that mask or cancel ambient sounds, but are not worn. For example, sound masking can be done by devices that emit "white noise." Sound cancelling can be done by devices that emit sound with wave patterns that are the inverse of the wave patterns of ambient sounds. Such devices may be placed on a bed stand or may be incorporated into a sound-emitting pillow. Examples of devices in the prior art that appear to be in this category include U.S. Pat. Nos. 5,844,996 (Enzmann et al., 2001), 6,289,538 (Fidge, 2001), and 7,627,917 (Vandenbelt, 2009). Limitations of such devices can include: such devices do not block ambient sounds as well as wearable devices can; such devices emit sound that can disturb other people who share the same bed or bedroom; the sound masking or sound cancelling benefits of such devices is thwarted when a sleeper's ears are covered by a blanket (on top) or a (non-sound-emitting) pillow below; and a sound-emitting pillow can be uncomfortable if a sleeper rests their head directly on a speaker, but can be muffled if a sleeper rests their head on part of the pillow away from the speaker.

3. Headphones or Ear Buds that Mask or Cancel Ambient Sounds that are not Designed to be Worn while Sleeping The prior art also includes studio-style headphones or insertable ear buds that are worn to mask or cancel ambient sounds, but are not designed to be worn while sleeping. Such devices generally include some rigid components, such as electromagnetic speakers that cover the sleeper's ears and/or rigid structures that span the sleeper's head to connect the speakers. Examples of devices in the prior art that appear to be in this category include U.S. Pat. Nos. 3,939,310 (Hodges, 1976), 4,070,553 (Hass, 1978), 4,110,583 (Lepper, 1978), 4,173,715 (Gosman, 1979), 4,424,880 (Murayama et al., 1984), 5,022,486 (Miura et al., 1991), 5,631,965 (Chang et al., 1997), 5,824,967 (Zwislocki, 1998), 5,953,434 (Boyden, 1999), 6,014,345 (Schmadeka, 2000), 6,301,367 (Boyden et al., 2001), 6,567,525 (Sapiejewski, 2003), 6,920,228 (Redmer et al., 2005), 7,110,563 (Bergere, 2006), 7,248,705 (Mishan, 2007), 7,268,669 (McEvoy, 2007), and 7,340,071 (Huang, 2008), and U.S. Patent Application No. 20070280484 (Anderson, 2007). Limitations of such devices can include: such devices with rigid components are uncomfortable, and even potentially unsafe, when the rigid components press against a sleeper's ears, head, or face—especially when they sleep on their side or toss and turn; the sound-emitting portions of such devices can be dislocated from a sleeper's ears as a sleeper tosses and turns, resulting in loss of sound masking or cancellation benefits; and such devices can break as a sleeper tosses and turns.

4. Wearable Devices with a Sound-Emitting Acoustic Tube Fitting into a Person's Ear that are not Designed to be Worn while Sleeping The prior art also includes sound-emitting acoustic tubes that fit into a person's ear, but that are not designed to be worn while sleeping. Examples of such devices include the acoustic tube headphones that have been common in the passenger sections of commercial aircraft. Examples of devices in the prior art that appear to be in this category include U.S. Pat. Nos. 3,539,031 (Scanlon, 1970), 3,899,044 (Stumpf et al., 1975), 4,261,432 (Gunterman, 1981), 4,347,911 (Bertagna et al., 1982), and 4,554,993 (Houng, 1985). Such devices are poorly suited for use while sleeping. Limitations of such devices for use while sleeping can include: the tubes dangling from both ears can easily become tangled as a sleeper tosses and turns; and the earpieces are uncomfortable when one sleeps on one's side and may even pose a safety risk if they are pushed into the ear canal by the pressure of a pillow.

5. Wearable Soft Headband (or Hat) that Contains Speakers Placed Over the Ears and can be Worn while Sleeping The prior art also includes some, although not many, soft headbands, hats or other articles of clothing that can be worn while sleeping and which contain speakers placed over the ears to mask or cancel ambient sounds. Examples of devices in the prior art that appear to be in this category include U.S. Pat. Nos. 4,776,044 (Makins, 1988), 4,864,619 (Spates, 1989), 5,303,426 (Jones, 1994), 5,625,903 (Schultz et al., 1997), and 7,394,912 (Whipple, 2008), and U.S. Patent Application No. 20080304691 (Lai, 2008). Limitations of such devices can include: electromagnetic speakers have rigid parts, so there is a disadvantageous tradeoff between having too little padding (so that the speakers press uncomfortably into one's ear) vs. having too much padding (so that the sound masking or cancelling benefits are greatly reduced); problems with adjusting the location of the speakers to cover the ears of people with differently sized and shaped heads; and the speakers being pushed away from the sleeper's ears as the sleeper tosses and turns during the night.

Several of the limitations of prior art in these five categories are highlighted in the following quote from an actual product review by a consumer that appears on the Amazon.com website. This review was written by someone who purchased a pair of headphones that is intended to be worn while sleeping. In the interest of competitive courtesy, I have replaced the actual brand name of the headphones to which the reviewer refers with the generic phrase "PRODUCT NAME"—

"I still find it helpful to fall asleep while listening to soft music, familiar movies, or audio books. I go through headphones frequently . . . . The problem with all of the headphones I have tried to use while sleeping has to do most with comfort or lack thereof while I am sleeping on my side. Ear bud style headphones are definitely the least comfortable on my ears when lying on my side. Studio style headphones are generally what I use because they give me the least amount of pain, the problem with this is that awoken to find many a broken pair of headphones . . . . I would like to note that it is a bit annoying how when lying on my side, one side of the PRODUCT NAME are pushed up against my ear (making it sound good) while the other side has a much different, lighter sound (and more background noise coming through). This is to be expected with any pair of headphones but with the PRODUCT NAME and the way they fit, there can be a big difference in sound between ears when lying on one side." http://www.amazon.com/review/R2FYWZZ34R5SS3/ref=cm_cr_pr_viewpnt#R2FYWZZ34R5SS3

The consumer in this review highlights that ear buds or headphones that are not designed to be worn while sleeping can be very uncomfortable, especially when one sleeps on one's side. The rigid speakers (and headsets in studio style models) press against one's ear (and head) when the side of one's head presses against the pillow. This consumer review also highlights that even those headphones in the prior art that are specifically intended to be worn while sleeping can require some adjustment to align speakers with one's ears and, even after careful adjustment, the speakers can still shift away from one's ears as one tosses and turns during the night. The above consumer review comments on how annoying this can be. Finally, this consumer highlights that headphones with rigid parts can break as one tosses and turns during sleep. The invention that is discussed in the next section addresses these limitations of the prior art.

SUMMARY AND ADVANTAGES OF THIS INVENTION

This invention is a wearable sound-emitting device that masks or cancels annoying ambient sounds while one sleeps. This invention includes: a soft and stretchable member (such as a headband or hat) that covers one's ears; a sound-conducting tube that is woven, sewn, or otherwise integrated into the soft and stretchable member and that emits sounds that mask or cancel annoying ambient sounds; and a sound-producing member that is either part of the soft and stretchable member or external to it.

This invention has several advantages over prior art. For example, advantages of this invention over wearable devices that block (but do not mask or cancel) ambient sounds include: this invention enables blocking, masking, and cancelling ambient sounds; and this invention has no rigid components covering the sleeper's ears that can become uncomfortable when a person sleeps on their side. Advantages of this invention over devices that mask or cancel ambient sounds that are not worn include: this device can block (as well as mask or cancel) ambient sounds; and this device can work for masking tinnitus as well as ambient sounds.

Further, advantages of this invention over headphones or ear buds that are not designed to be worn while sleeping include: this invention has no rigid components over a sleeper's ears that can be uncomfortable or unsafe when someone sleeps on their side; this invention has a relatively wide sound-emitting area to accommodate people with different size heads; and this invention stretches to gently cling to a person's head to reduce dislocation of its sound-emitting area away from the sleeper's ears.

Further, advantages of this invention over wearable devices with sound-emitting acoustic tubes fitting into a person's ear include: avoiding dual tubes (or, in some embodiments, any tubes) dangling from the person's head that could become tangled; and avoiding uncomfortable and potentially unsafe tubes fitting into one's ears when one sleeps on one's side. Advantages of this invention over a wearable soft headband (or hat) containing speakers placed over the ears include: this invention has no speakers with rigid components pressing against one's ears when the side of one's head presses against a pillow; this invention has a relatively wide sound-emitting area to accommodate people with different size and shape heads; and this invention stretches to gently cling to a person's head to reduce dislocation of its sound-emitting area away from the sleeper's ears.

INTRODUCTION TO THE FIGURES

These figures show examples of how this invention may be embodied, but they do not limit the full generalizability of the claims.

DETAILED DESCRIPTION OF THE FIGURES

The following figures show some examples of how this invention may be embodied. These are only some of the various ways in which this invention may be embodied and do not limit the full generalizability of the claims.

Figure 1:
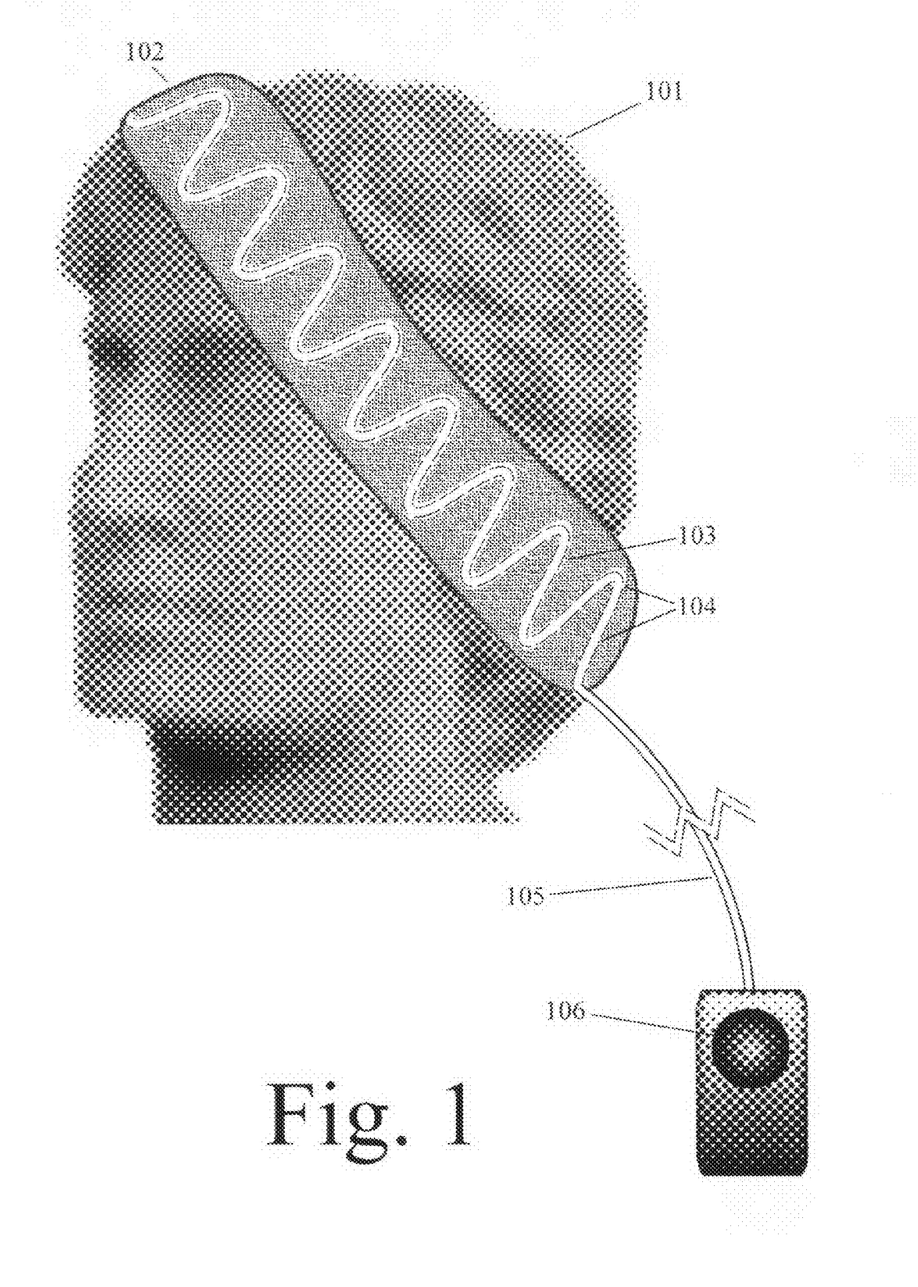
FIG. 1 shows an oblique-angle semi-transparent view of one embodiment of this invention with a stretchable headband and an air-filled sound-conducting tube within the headband.

FIG. 1 shows an oblique-angle semi-transparent view of one embodiment of this invention featuring a soft and stretchable headband, 102, that is worn around a person's head, 101, roughly from the peak of their forehead to the nape of their neck. In this manner, the headband covers the person's ears. In various examples, headband 102 may be made from material selected from the group consisting of acetate, acrylic, cotton, linen, neoprene, nylon, polyester, rayon, silk, spandex, wool, or a combination thereof. In FIG. 1, headband 102 is shown as semi-transparent so that one can see how sound-conducting tube 103 is configured within it. In actuality, sound-conducting tube 103 may not be visible when viewing the headband because the tube may be hidden within the fabric of the headband.

In the embodiment of this invention that is shown in FIG. 1, headband 102 contains a flexible sound-conducting tube 103 that is sewn into the headband in a sinusoidal configuration. The sinusoidal configuration of tube 103 allows the headband to stretch circumferentially around the person's head, even if the tube itself is made from material that does not stretch. In this example, tube 103 is sewn into the fabric of headband 102. In other examples, sound-conducting tube 103 may be woven, adhered, looped, tied or otherwise integrated within or onto headband 102.

In various examples, sound-conducting tube 103 may be made from material selected from the group consisting of ethylene propylene diene monomer (EPDM), latex, silicone, polyvinyl chloride, and polyurethane. In various examples, the diameter of tube 103 may be within the range of ⅛" to ⅜", the wall thickness of tube 103 may be within the range of 0.024" to 0.031", the durometer of tube 103 may be within the range of 35 to 85 shore, and the length of tube 103 may be within the range of 1 inch to 2 feet.

In this embodiment, sound that is conducted through flexible sound-conducting tube 103 is emitted from the tube through holes, such as those labeled 104, along the walls of the tube. In another example, the sound-conducting tube may contain a liquid instead of air; and sound may be emitted from the tube through diaphragms at various locations along the wall of the tube instead of through holes. In another example, there may be a sound-conducting channel formed by sound-resisting layers within the headband, instead of a separate sound-conducting tube within the headband. Holes in the channel could let sonic energy escape the channel at different locations along the headband.

In this embodiment, the source of the sound is a sound-producing member, 106, that is external to the headband. Sound from this sound-producing member 106 is conducted to sound-conducting tube 103 through an extension 105 of the sound-conducting tube from the sound-producing member to the headband. In an example, this extension 105 may be a flexible tube, 3 to 6 feet in length, with a relatively thick wall and no holes so as to maximize conduction and minimize escape of sonic energy along its span. In this example, sound-producing member 106 includes an electromagnetic speaker. This speaker is in flowable communication with the air inside extension 105 and, thus, the interior of sound-conducting tube 103. In another example wherein tube 103 and extension 105 are filled with a liquid, the speaker can be in flowable communication with a diaphragm at the end of extension 105. The diaphragm transduces sonic energy from the air near the speaker to the liquid inside extension 105 and tube 103.

The sound produced by sound-producing member 106 may be selected from the group consisting of: white noise, pink noise, music, pre-recorded loops of soothing sounds, and waveforms created in real time to cancel out ambient sounds. In an example involving noise cancellation, ambient sounds would be detected by a nearby microphone, waveforms would be created in real time to specifically cancel out the waveforms of those ambient sounds, and these waveforms would be produced by the sound-producing member.

In this embodiment, headband 102 and sound-producing member 106 are presented as part of a combined product sold by the same vendor. In another example, the headband and sound-producing member could be separate, but technologically compatible, products that are sold by different vendors. In this example, sound-producing member 106 is approximately 3 to 6 feet away from headband 102 and linked to sound-conducting tube 103 by extension 105 of the tube. In another example, the sound-producing member may be integrated into, or attached onto, the headband itself and no connecting tube would be required. In this example, there is one sound-producing member and one sound-conducting tube. In another example, there may be two or more sound-producing members connected to two or more sound-conducting tubes.

This invention has several advantages over sound masking and cancelling devices in the prior art. We will first discuss advantages of this present invention over devices in the prior art to mask or cancel ambient sounds while sleeping that are not worn on the head. As one advantage, in addition to masking and cancelling ambient sounds, a device that covers the ears can also block ambient sounds. A device that is not worn on the head and does not cover the ears cannot block ambient sounds in this manner. As a second advantage, it is much easier to cancel ambient sounds from multiple directions with a device that emits sounds close to a sleeper's ears than it is with a device that emits sounds some distance away from the sleeper's ears. As a third advantage, a sound-emitting device that is worn close to a sleeper's ears can achieve sound masking and cancelling with a much lower level of sonic energy than is required using a sound-emitting device that is some distance away from a wearer's ear. Achieving sound masking or cancelling with lower energy levels is particularly important when there is another person in the same room who would be disturbed by the loud sound emitted by a device that is not worn.

The embodiment of this invention shown in FIG. 1 also demonstrates advantages of this invention over prior art that is worn on the head to mask or cancel ambient sounds while one is sleeping. With respect to comfort, it is much more comfortable to have a soft stretchable headband containing a curving flexible tube pressing against one's ear (as in this invention) than to have a rigid electromagnetic speaker pressing against one's ear (as in the prior art). With respect to loss of sound coverage over the ear, a sound-conducting tube with multiple holes can emit sound over a relatively wide area in order to provide sonic coverage for the ears for people with different size heads and to maintain sonic coverage for the ears while people toss and turn during the night. With respect to breakage, the embodiment of this invention shown in FIG. 1 does not have any breakable rigid parts in the headband portion that is worn on the head.

Figure 2:
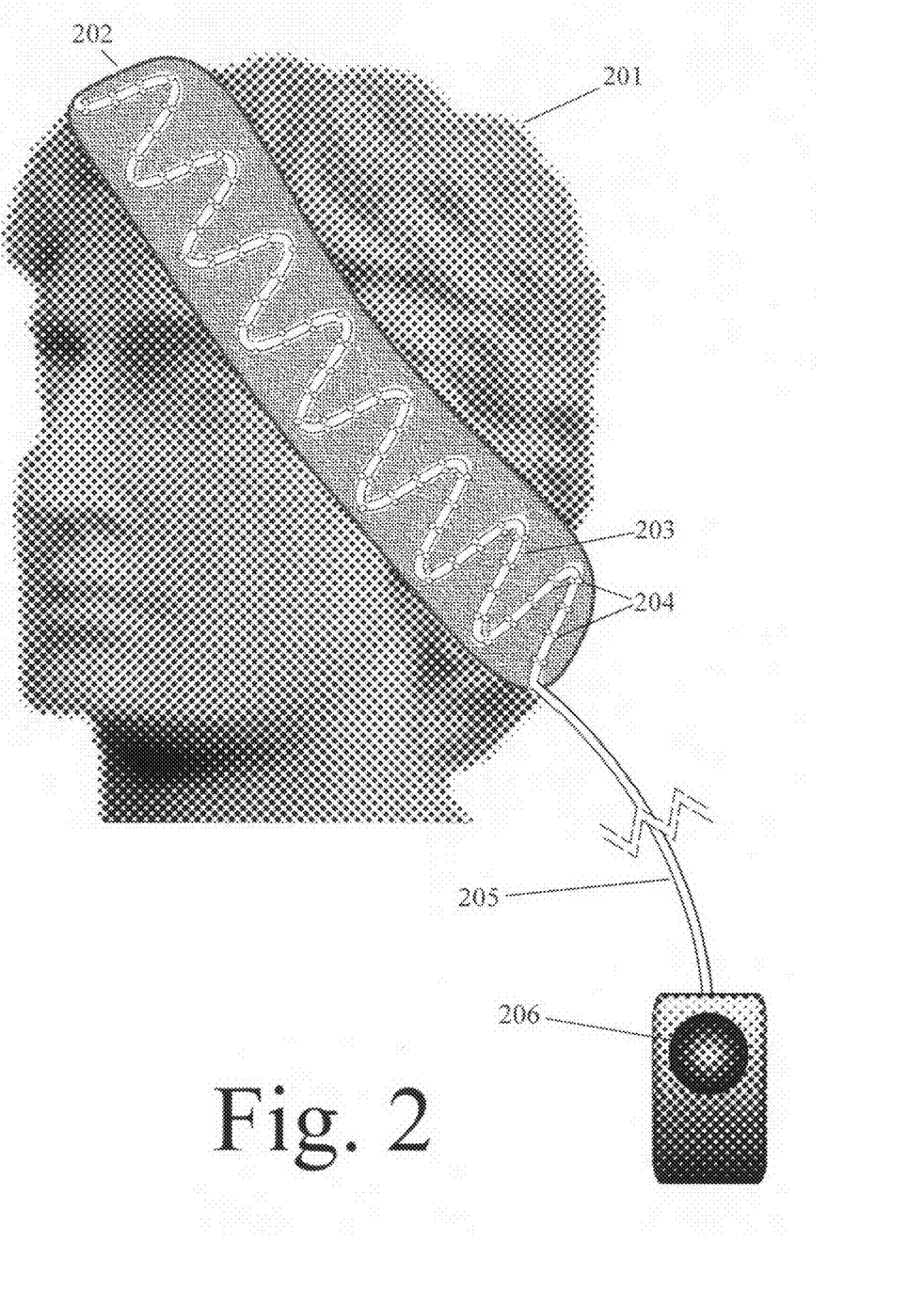
FIG. 2 shows a similar embodiment, except that the sound-conducting tube is filled with a liquid instead of air.

FIG. 2 shows an oblique-angle semi-transparent view of another headband-style embodiment of this invention that is similar to that shown in FIG. 1 except that: the sound-conducting tube 203 is filled with a liquid instead of air; and sound is emitted from the sound-conducting tube 203 through small diaphragms, including those labeled 204, along the walls of tube 203. In various examples, the liquid inside tube 203 may be water with an additive to resist microbial growth or some other non-toxic liquid that resists microbial growth. A liquid-filled tube may be a more efficient conductor of sonic energy than an air-filled tube for certain frequencies or when the tube is squeezed by pressure from the wearer's head on a pillow. As initially discussed above, in the case of a liquid-filled sound-conducting tube, a speaker in sound-producing member 206 could be in flowable communication with a diaphragm at the end of extension 205. This diaphragm would transduce sonic energy from the air near the speaker to the liquid inside extension 205 and tube 203.

Figure 3:
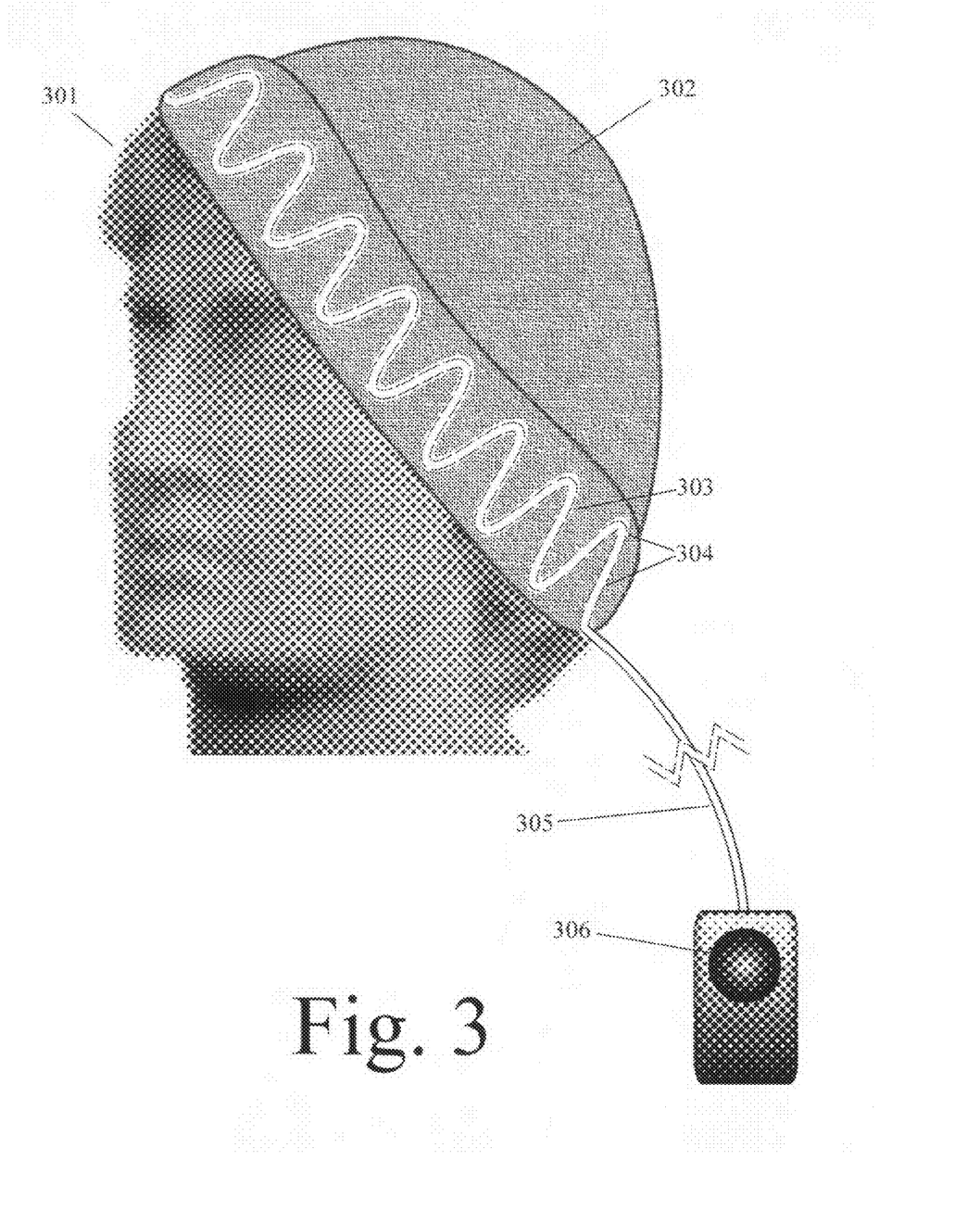
FIG. 3 shows another embodiment of this invention with a hat instead of a headband.

FIG. 3 shows an oblique-angle semi-transparent view of another embodiment of this invention that is the same as the embodiment shown in FIG. 1, except that now the wearable member is an entire hat 302 instead of just a headband. As in the embodiment shown in FIG. 1, sound produced by a sound-producing member 306 is conducted by an extension tube 305 to a sinusoidal sound-conducting tube 304 and emitted via holes 304 in the tube in the vicinity of the person's ears. A hat-based embodiment may conform to and cling to the wearer's head 301 better than a headband alone. This may be provide greater resistance to shifting when a person tosses and turns while they sleep and thereby be better for keeping the sound-emitting portion of the device over the person's ears.

Figure 4:
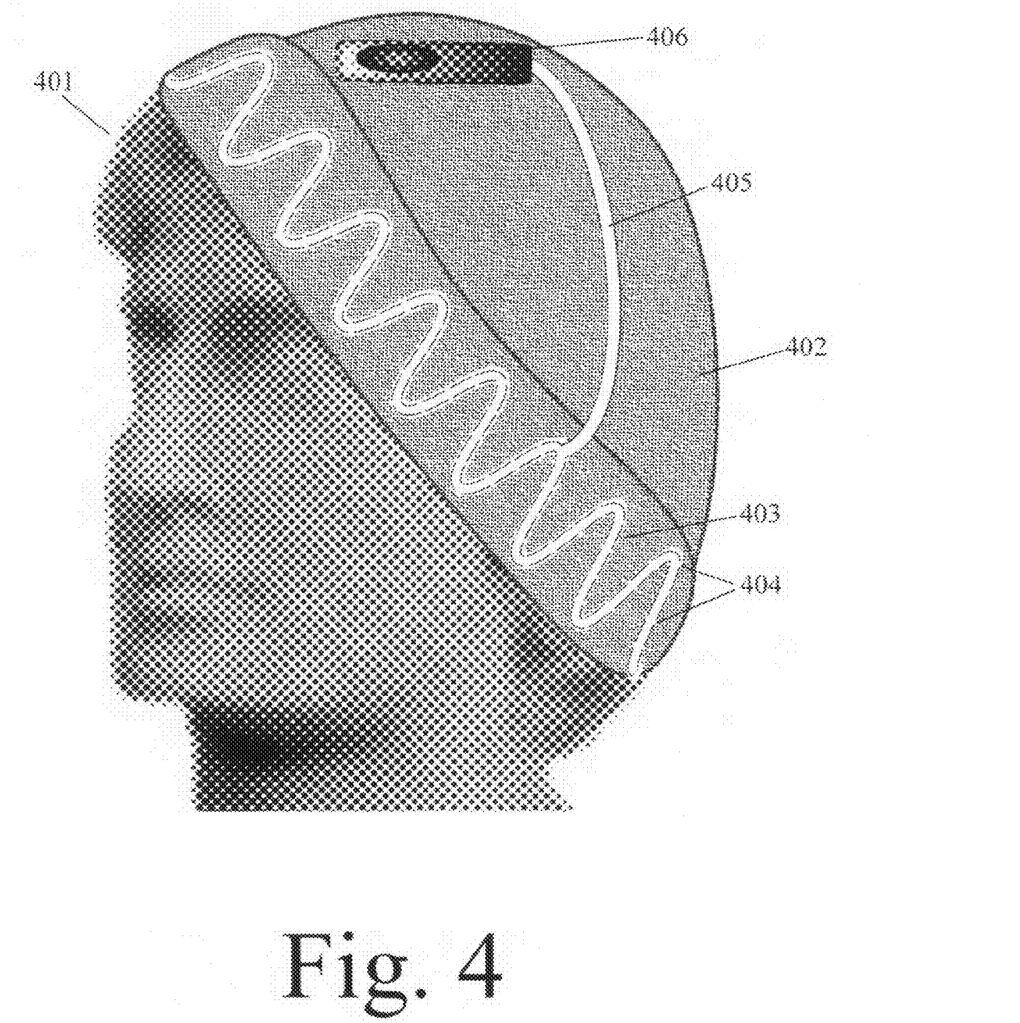
FIG. 4 shows another embodiment of this invention wherein a sound-producing member is integrated into a hat.

FIG. 4 shows an oblique-angle semi-transparent view of another embodiment of this invention. This embodiment that is the same as the hat embodiment that is shown in FIG. 3, except that now the sound-producing member 406 is integrated into the hat 402 instead of being external. One advantage of integrating the sound-producing member 406 into hat 402 is that this eliminates the need for an extension tube from the external sound-producing member to the wearable member that could become tangled as a person tosses and turns in their sleep. In an example, the sound-producing member may be contained in a woven compartment in hat 402 and be detachable for washing the hat. In an example, the sound-producing member may be integrated into the hat at a location near the top of the person's head wherein this location is unlikely to come into contact with a pillow or other sleeping surface. In such a location, even if the sound-producing member contains rigid components such as electromagnetic speakers, it will not cause discomfort by pressing against one's ears as is the case with devices with speakers over the ears in the prior art.

Figure 5:
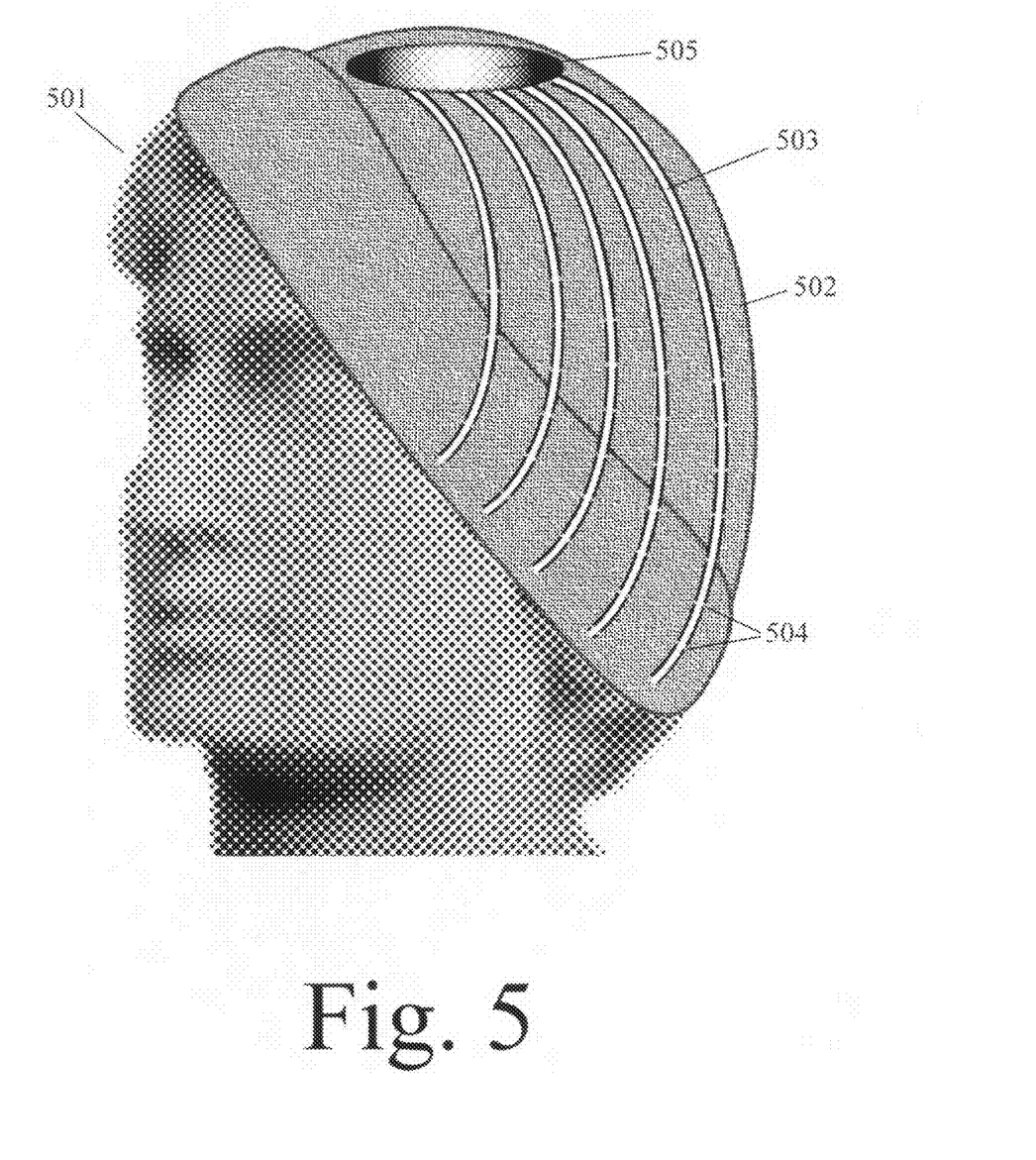
FIG. 5 shows another embodiment of this invention with multiple sound-conducting tubes within a hat.

FIG. 5 shows an oblique-angle semi-transparent view of another hat-style embodiment of this invention. In this embodiment, there are multiple sound-conducting tubes, including tube 503, that radiate outwards in spokes from sound-producing member 505 at the top of the hat. Having multiple tubes configured as radial spokes, as in this embodiment, is another way to integrate sound-conducting tubes into a wearable member, such as hat 502, that does not restrict circumferential stretching of that member around the person's head 501. In this example, only those portions of the tubes that are in the vicinity of the person's ears have holes, such as those labeled 504, that emit sound. This tube configuration can allow more uniform sound levels around the circumference of the band of the hat than is possible with a single sinusoidal tube. More uniform sound levels around the band of the hat can, in turn, provide more uniform sound masking and cancellation for people with different size heads or when the hat shifts as a person tosses and turns during their sleep.

I claim:

1. A wearable sound-emitting device to mask and/or cancel ambient sounds, comprising:
   a wearable, stretchable, and soft member; wherein this member is worn around a portion of a person's head; wherein the wearable member includes at least one ear-covering portion;
   wherein this ear-covering portion is stretchable and soft; wherein this ear-covering portion is held in stretched tension between at least two points that are separated by the diameter of the ear; wherein this ear-covering portion clings to the ear due to this stretched tension so that it is not dislocated away from the ear as the person tosses and turns in their sleep;
   one or more sound-conducting tubes or channels; wherein these tubes or channels are filled with a gas and/or liquid; and wherein these tubes or channels are woven, sewn, adhered, looped, tied or otherwise integrated with or onto the ear-covering portion; wherein at least one of these sound-conducting tubes or channels has multiple holes and/or diaphragms along its wall that allow sonic energy to escape at selected locations along its wall; and wherein at least two of these holes and/or diaphragms are between 0.1 mm and 30 mm in diameter; and one or more sound-producing members; wherein these sound-producing members are in sound-conducting communication with the interior of the one or more sound-conducting tubes or channels; and wherein sound from the sound-producing members is conducted through the one or more sound-conducting tubes or channels to the person's ears in order to mask and/or cancel ambient sounds.

2. The wearable sound-emitting device in claim 1 wherein at least one of the sound-conducting tubes or channels has multiple holes that are formed by: one or more holes made along a tube wall; one or more holes at the end of a tube; and/or one or more holes at the end of a tube branch.

3. The wearable sound-emitting device in claim 1 wherein the one or more sound-conducting tubes or channels are in a configuration that does not substantively interfere with the ability of the wearable member to stretch around the person's head.

4. The wearable sound-emitting device in claim 1 wherein the one or more sound-conducting tubes or channels have longitudinal axes that are substantially parallel with the surface of the person's head as they span the person's ear.

5. The wearable sound-emitting device in claim 1 wherein the sound produced by the sound-producing members is selected from the group consisting of: white noise, pink noise, music, pre-recorded loops of natural sounds, and sounds configured to cancel out ambient sounds.

6. The wearable member in claim 1 wherein this member is selected from the group consisting of: headband, hat, cap, and ski mask.

7. The wearable sound-emitting device in claim 1 wherein the wearable member is made from material selected from the group consisting of acetate, acrylic, cotton, linen, neoprene, nylon, polyester, rayon, silk, spandex, wool, or a combination thereof.

8. The wearable sound-emitting device in claim 1 wherein the one or more sound-conducting tubes or channels: have with a diameter within the range of 1/8"-3/8"; have a wall thickness within the range of 0.024"-0.031"; have a durometer within the range of 35-85 shore; have a length within the range of 2 inches to 2 feet; and are made from material selected from the group consisting of ethylene propylene diene monomer (EPDM), latex, silicone, polyvinyl chloride, and polyurethane.

9. A wearable sound-emitting device to mask and/or cancel ambient sounds, comprising:

a wearable, stretchable, and soft member; wherein this member is worn around a portion of a person's head; wherein the wearable member includes at least one ear-covering portion;

wherein this ear-covering portion is stretchable and soft; wherein this ear-covering portion is held in stretched tension between at least two points that are separated by the diameter of the ear; wherein this ear-covering portion clings to the ear due to this stretched tension so that it is not dislocated away from the ear as the person tosses and turns in their sleep;

one or more sound-conducting tubes or channels; wherein these tubes or channels are filled with a gas and/or liquid; wherein these tubes or channels are woven, sewn, adhered, looped, tied or otherwise integrated with or onto the ear-covering portion; wherein at least one of these sound-conducting tubes or channels has multiple holes and/or diaphragms along its wall that allow sonic energy to escape at selected locations along its wall; wherein at least two of these holes and/or diaphragms are between 0.1 mm and 30 mm in diameter and at least one of the areas spanned by these selected locations is at least 10 mm in length; and one or more sound-producing members; wherein these sound-producing members are in sound-conducting communication with the interior of the one or more sound-conducting tubes or channels; and wherein sound from the sound-producing members is conducted through the one or more sound-conducting tubes or channels to the person's ears in order to mask and/or cancel ambient sounds.

10. The wearable sound-emitting device in claim 9 wherein the one or more sound-conducting tubes or channels are in a configuration that does not substantively interfere with the ability of the wearable, stretchable, and soft member to stretch around the person's head.

11. The wearable sound-emitting device in claim 9 wherein the one or more sound-conducting tubes or channels have longitudinal axes that are substantially parallel with the surface of the person's head as they span the person's ear.

12. The wearable sound-emitting device in claim 9 wherein the sound produced by the sound-producing members is selected from the group consisting of: white noise, pink noise, music, pre-recorded loops of natural sounds, and sounds configured to cancel out ambient sounds.

13. The wearable, stretchable, and soft member in claim 9 wherein this member is selected from the group consisting of: headband, hat, cap, and ski mask.

14. The wearable sound-emitting device in claim 9 wherein the wearable, stretchable, and soft member is made from material selected from the group consisting of acetate, acrylic, cotton, linen, neoprene, nylon, polyester, rayon, silk, spandex, wool, or a combination thereof.

15. The wearable sound-emitting device in claim 9 wherein the one or more sound-conducting tubes or channels: have with a diameter within the range of 1/8"-3/8"; have a wall thickness within the range of 0.024"-0.031"; have a durometer within the range of 35-85 shore; have a length within the range of 2 inches to 2 feet; and are made from material selected from the group consisting of ethylene propylene diene monomer (EPDM), latex, silicone, polyvinyl chloride, and polyurethane.

16. A wearable sound-emitting device to mask and/or cancel ambient sounds, comprising:

a wearable, stretchable, and soft member; wherein this member is worn around a portion of a person's head; wherein the wearable member includes at least one ear-covering portion;

wherein this ear-covering portion is stretchable and soft; wherein this ear-covering portion is held in stretched tension between at least two points that are separated by the diameter of the ear; wherein this ear-covering portion clings to the ear due to this stretched tension so that it is not dislocated away from the ear as the person tosses and turns in their sleep;

one or more sound-conducting tubes or channels; wherein these tubes or channels are filled with a gas and/or liquid; wherein these tubes or channels are woven, sewn, adhered, looped, tied or otherwise integrated with or onto the ear-covering portion; wherein at least one of these sound-conducting tubes or channels has multiple holes and/or diaphragms along its wall that allow sonic energy to escape at selected locations along its wall; wherein at least two of these holes and/or diaphragms are between 0.1 mm and 30 mm in diameter and at least one of the areas spanned by these selected locations is at least 10 mm in length; wherein the one or more sound-conducting tubes or channels are in a configuration that does not substantively interfere with the ability of the wearable member to stretch around the person's head; and wherein the one or more sound-conducting tubes or channels have longitudinal axes that are substantially parallel with the surface of the person's head as they span the person's ear;

one or more sound-producing members; wherein these sound-producing members are in sound-conducting communication with the interior of the one or more sound-conducting tubes or channels; and wherein sound from the sound-producing members is conducted through the one or more sound-conducting tubes or channels to the person's ears in order to mask and/or cancel ambient sounds.

17. The wearable sound-emitting device in claim 16 wherein the sound produced by the sound-producing members is selected from the group consisting of: white noise, pink noise, music, pre-recorded loops of natural sounds, and sounds configured to cancel out ambient sounds.

18. The wearable sound-emitting device in claim 16 wherein the one or more sound-producing members are integrated into or attached onto the wearable, stretchable and soft member.

19. The wearable sound-emitting device in claim 16 wherein the wearable, stretchable and soft member is made from material selected from the group consisting of acetate, acrylic, cotton, linen, neoprene, nylon, polyester, rayon, silk, spandex, wool, or a combination thereof.

20. The wearable sound-emitting device in claim 16 wherein the one or more sound-conducting tubes or channels: have with a diameter within the range of $\frac{1}{8}$"-$\frac{3}{8}$"; have a wall thickness within the range of 0.024"-0.031"; have a durometer within the range of 35-85 shore; have a length within the range of 2 inches to 2 feet; and are made from material selected from the group consisting of ethylene propylene diene monomer (EPDM), latex, silicone, polyvinyl chloride, and polyurethane.

* * * * *